United States Patent [19]

Lein

[11] Patent Number: 4,981,789
[45] Date of Patent: Jan. 1, 1991

[54] ONE-STEP ENZYMATIC CONVERSION OF CEPHALOSPORIN C AND DERIVATIVES TO 7-AMINOCEPHALOSPORANIC ACID AND DERIVATIVES

[75] Inventor: Joseph Lein, Deer Harbor, Wash.

[73] Assignee: Merck & Co., Inc., Rahway, N.J.

[21] Appl. No.: 136,227

[22] Filed: Dec. 21, 1987

Related U.S. Application Data

[63] Continuation-in-part of Ser. No. 27,578, Mar. 18, 1987, abandoned.

[51] Int. Cl.$^5$ .............................................. C12P 35/02
[52] U.S. Cl. ..................................... 435/51; 435/227; 435/228; 435/830
[58] Field of Search ............... 435/47, 51, 227, 228, 435/830, 837, 49

[56] References Cited

U.S. PATENT DOCUMENTS

| | | | |
|---|---|---|---|
| 3,144,395 | 8/1964 | Murao et al. | 435/51 |
| 3,239,394 | 3/1966 | Walton et al. | 435/51 |
| 3,522,250 | 7/1970 | Kerwin et al. | 435/51 |
| 3,565,763 | 2/1971 | Cadmus et al. | 435/830 |
| 3,749,641 | 7/1973 | Takahashi et al. | 435/51 |
| 3,801,458 | 4/1974 | Fiides et al. | 435/51 |
| 3,821,081 | 6/1974 | Abe et al. | 435/51 |
| 3,880,713 | 4/1975 | Fleming et al. | 435/51 |
| 3,915,798 | 10/1975 | Yamaguchi et al. | 435/51 |
| 3,930,949 | 1/1976 | Kutzback et al. | 435/51 |
| 3,945,888 | 8/1976 | Takahashi et al. | 435/51 |
| 3,960,662 | 6/1976 | Matsuda et al. | 435/51 |
| 3,962,036 | 6/1976 | Liersch et al. | 435/51 |
| 4,141,790 | 2/1979 | Niwa et al. | 435/51 |
| 4,774,179 | 9/1988 | Ichikawa et al. | 435/51 |

FOREIGN PATENT DOCUMENTS

| | | | |
|---|---|---|---|
| 3447023 | 6/1986 | Fed. Rep. of Germany . | |
| 0275901-A2 | 7/1988 | Fed. Rep. of Germany . | |
| 2241557 | 4/1975 | France . | |
| 50-107186 | 8/1975 | Japan . | |
| 52-082791 | 2/1977 | Japan . | |
| 52-128293 | 10/1977 | Japan . | |
| 53-094093 | 8/1978 | Japan . | |
| 54-110394 | 8/1979 | Japan . | |
| 0085298 | 7/1981 | Japan | 435/51 |
| 58-190399 | 7/1983 | Japan . | |
| 6121097 | 7/1984 | Japan . | |
| 0110292 | 6/1985 | Japan | 435/51 |
| 61-152286 | 7/1986 | Japan . | |
| 63-74488 | 4/1988 | Japan . | |
| 2142336A | 1/1985 | United Kingdom . | |

OTHER PUBLICATIONS

Dev. Ind. Microbiol. 5, 349 (1964).
Agric. Biol. Chem. 54, 1561–67 (1981).
Process Biochem., 11 21 (1976).

*Primary Examiner*—Charles F. Warren
*Assistant Examiner*—Gail Poulos
*Attorney, Agent, or Firm*—Raymond M. Speer; Hesna J. Pfeiffer

[57] ABSTRACT

A process for the one-step conversion of cephalosporin C and derivatives thereof to the corresponding 7-aminocephalosporanic acid and derivatives comprising treating said cephalosporin C and derivatives with a cephalosporin C amidase derived from *Arthrobacter viscosus* ATCC 53594, or from any cephalosporin C amidase producing, or potentially producing descendants thereof, or from any expression of the genetic material of said *Arthrobacter viscosus* ATCC 53594, or any cephalosporin C amidase producing, or potentially producing descendants thereof.

3 Claims, No Drawings

ONE-STEP ENZYMATIC CONVERSION OF CEPHALOSPORIN C AND DERIVATIVES TO 7-AMINOCEPHALOSPORANIC ACID AND DERIVATIVES

REFERENCE TO RELATED APPLICATIONS

This is a continuation-in-part of application Ser. No. 027,578, filed Mar. 18, 1987, now abandoned.

BRIEF SUMMARY OF THE INVENTION

The present invention relates to a process for the one-step conversion of cephalosporin C and derivatives thereof to the corresponding 7-aminocephalosporanic acid (7-ACA) and derivatives comprising treating said cephalosporin C and derivatives with a cephalosporin C amidase derived from *Arthrobacter viscosus* ATCC 53594, or from any cephalosporin C amidase producing, or potentially producing descendants thereof, or from any expression of the genetic material of said *Arthrobacter viscosus* ATCC 53594, or any cephalosporin C amidase producing, or potentially producing descendants thereof. Thus, the present invention involves enzymatic cleavage (deacylation) of the 7-aminoadipoyl sidechain of cephalosporin C. Since the 7-aminoadipoyl sidechain is removed by cleavage of an amide linkage, the particular enzyme which accomplishes the conversion is referred to herein as an amidase. Cephalosporin C itself is a fermentation product which is the starting point for nearly all currently marketed cephalosporins. However, synthetic manipulation to produce these various commercial cephalosporins basically starts with the 7-aminocephalosporanic acid, which must be derived from the cephalosporin C by cleavage of the 7-aminoadipoyl sidechain.

Currently, the method of choice in the art for cleaving the 7-aminoadipoyl sidechain is chemical. The basic imino-halide process requires blocking of the amino and carboxyl groups on the 7-aminoadipoyl sidechain, and several methods for accomplishing this are currently used. However, as presently employed, the chemical cleavage process has serious disadvantages. Among these are the requirements of a multi-step and complex process, extremely low operating temperatures expensive reagents, significant quantities of process by-products resulting in effluent treatment problems, and purification of a highly impure starting material before chemical treatment begins. Consequently, there has been an ongoing search for a microbiological or fermentative process which would achieve enzymatic deacylation of cephalosporin C to provide 7-aminocephalosporanic acid on a more economic basis than the chemical process currently in use.

However, this search for a successful microbiological process has largely proved futile. This is a result, as is made clear in the literature, of the structure, and especially the stereochemistry, of the aminoadipoyl sidechain of the cephalosporin C molecule, since penicillin has been successfully deacylated by enzymatic cleavage using penicillin acylase produced by a variety of microorganisms. Reports of successful one-step enzymatic deacylation of cephalosporin C in the literature, on the other hand, are often unreproducible or provide only very marginal yields. Moreover, the isolation of 7-ACA as a reaction product does not require that the conversion from cephalosporin C to 7-ACA proceed by way of only one enzymatic transformation, i.e., that it be truly one-step. Other enzymes could possibly transform the cephalosporin C into other compounds which could then be susceptible to cleavage by cephalosporin C amidase enzyme. For example, Meiji in Japanese Patent Publication No. 53-94093 (see below) described isolation of what they thought to be cephalosporin C amidase, only to find that the transformation from cephalosporin C to 7-ACA involved the prior enzymatic conversion of cephalosporin C to glutaryl-7-ACA by a D-amino acid oxidase. The intermediate product, glutaryl-7-ACA, was then cleaved by the amidase enzyme to produce 7-ACA. See Shibuya et al., Agric. Biol. Chem., 45, 1561–1567 (1981).

Thus, it was a surprising result to be able to obtain a strain of *Arthrobacter viscosus* that could provide significant yields of 7-aminocephalosporanic acid by efficient one-step enzymatic deacylation of cephalosporin C. Strong evidence that one-step cleavage has been achieved resides in the one to one molar ratio of the 7-ACA and aminoadipic acid products isolated from incubation of cephalosporin C with enzyme from *Arthrobacter viscosus*, as is described further below.

A summary of the literature which describes these ongoing efforts to achieve enzymatic cleavage of cephalosporin C is set out below.

1. One-Step Enzymatic Deacylation: Ceph C→7-ACA

| | |
|---|---|
| Dev. Ind. Microbial., 5, 349 (1964) U.S. Pat. No. 3,239,394 Walton (Merck) Soil enrichment method of screening and selecting for microorganisms | Achromobacter, Brevibacterium, Flavobacterium |
| Jap. Pat. Pub. 53-94093 (1978) Goi et al. (Meiji) | Pseudomonas sp. BN-188 |
| Jap. Pat. Pub. 52-143289 (1977) U.S. Pat. No. 4,141,790 (Meiji) | Aspergillus sp. Alternaria sp. |
| Jap. Pat. Pub. 61-21097 (1986) Ichikawa et al. (Asahi) | Pseudomonas Sp. SE-83 (new species) |
| Fr. Pat. 2,241,557 (1975) (Aries) | Bacillus cereus var. fluorescens |
| Ger. Pat. 3,447,023 (1986) (Hoechst) In the presence of α-keto acids; enzyme is D-amino acid transaminase | Bacillus licheniformis |

2. One-Step Enzymatic Deacylation: Penicillin→6-APA

| | |
|---|---|
| Jap. Pat. Pub. 58-190399 (Shionogi) | Bacillis megaterium var. penicilliticum |

3. Two-Step Enzymatic Deacylation: Ceph C→7-ACA

| | |
|---|---|
| U.S. Pat. No. 3,960,662 Agric. Biol. Chem. 45, 1561-67 (1981) Fuijii et al. (Toyo Jozo) Deamination with D-amino acid oxidase followed by deacylation | Pseudomonos sp. |

4. Enzymatic Deacylation: GL-7-ACA*→7-ACA

| Jap. Pat. Pub. 52-128293 (1977) | Bacillus, |
| 53-86094 (1978) | Arthrobacter, |
| (Toyo Jozo) | Alcaligenes |

5. Enzymatic Deacylation: Other→7-ACA

| Process Biochem., 11, 21 (1976) | Bacillus |
| Fujii et al. (Toyo Jozo) | megaterium |
| phenylacetyl 7-ADCA | |
| → 7-ADCA | |
| U.S. Pat. No. 3,522,250 | Escherichia |
| Kerwin et al. (American Home Products) | coli |
| cephalothin → 7-ACA | |
| Jap. Pat. Pub. 50-107186 | Arthrobacter, |
| (Toyo Brewinq) | Bacillus, |
| phenylacetamido 7-ACA | Escherichia, |
| derivatives are | Kluyvera, |
| deacylated | Micrococcus, |
| | Nocardia, |
| | Proteus, |
| | Xanthomonas, |

6. Enzymatic Acylation: 7-ACA→Other

| Jap. Pat. Pub. 54-110394 | Arthrobacter |
| (Banyu) | viscosus |
| 7-ACA → cephapirin | |

*GL-7-ACA = glutaryl 7-ACA or deaminated ceph C

DETAILED DESCRIPTION OF THE INVENTION

In accordance with the present invention there is provided a process for the one-step conversion of cephalosporin C and derivatives thereof of the formula:

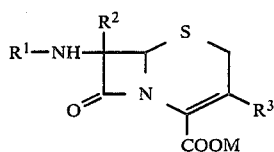  (I.)

where
$R^1$ is

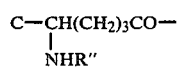

where R' and R" are independently hydrogen or a readily removable carboxyl or amino covering group, respectively; or any 7-position sidechain known in the art of cephalosporin antibacterial compounds;
$R^2$ is —H;
$R^3$ is —H or

or $CH_2R^4$, where $R^4$ is —H, —OH, or

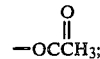

and

M is ⁻; —H; alkali metal or other pharmaceutically acceptable salt; pharmaceutically acceptable ester; or readily removable carboxyl covering group;
to a 7-aminocephalosporanic acid of the formula:

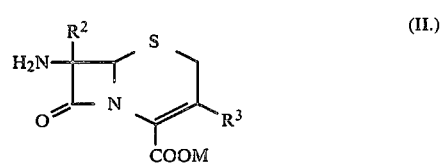  (II.)

COMPRISING:
treating a compound of Formula I with an enzyme, cephalosporin C amidase, capable of converting a compound of Formula I to a compound of Formula II in one step; said enzyme CHARACTERIZED BY having been derived from *Arthrobacter viscosus* ATCC 53594, or from any cephalosporin C amidase producing, or potentially producing descendants thereof, or from any expression of the genetic material of said *Arthrobacter viscosus* ATCC 53594, or any cephalosporin C amidase producing, or potentially producing descendants thereof.

In accordance with the present invention, there is also provided the microorganism *Arthrobacter vicosus* ATCC 53594, or any cephalosporin C amidase producinq, or potentially producing descendants thereof.

In accordance with the present invention there is further provided the genome of *Arthrobacter viscosus* ATCC 53594, or any cephalosporin C amidase producing, or potentially producing descendants thereof, or any portions of said genomes capable of expressing said cephalosporin C amidase.

In accordance with the present invention there is still further provided an enzyme, cephalosporin C amidase, capable of converting a compound of Formula I to a compound of Formula II in one step, said enzyme characterized by having been derived from *Arthrobacter viscosus* ATCC 53594, or from any cephalosporin C amidase producing, or potentially producing descendants thereof, or from any expression of the genetic material of said *Arthrobacter viscosus* ATCC 53594, or any cephalosporin C amidase producing, or potentially producing descendants thereof.

With reference to the compounds of Formula I above, the group $R^1$ defines, in a preferred embodiment, the moiety

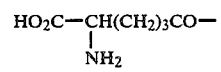

which is the cephalosporin C 7-aminoadipoyl sidechain. Here, both R' and R" are hydrogen. Since conventional covering groups for both the carboxyl and the amino groups of this aminoadipoyl sidechain are well known, R' and R" have also been defined to include readily removable carboxyl or amino covering groups, respectively.

The expression "readily removable carboxyl or amino covering groups" means a conventional substituent which takes the place of the hydrogen of the carboxyl or amino group and thereby prevents said group from reacting with any reagents employed in any subsequent synthesis. Such covering of the carboxyl and amino group is often necessary to prevent unwanted competing reactions involving said groups from taking place. Thus, all of these compounds are intermediates. The conventional covering substituent must also be "readily removable", by which is meant that it is selectively removable, i.e., it is not likely to be removed during the course of ordinary procedures which are to be carried out on the cephalo sporin nucleus and sidechains, while, on the other hand, it is likely to be removed by procedures which are not so harsh as to disturb the basic ring structure of the cephalosporin nucleus or unprotected substituents thereon.

$R^1$ also includes any 7-position sidechain known in the art of cephalosporin antibacterial compounds. Since the cephalosporin C amidase of the present invention is capable of recognizing the amide linkage and remaining portion of the cephalosporin C molecule as a whole, it is contemplated that other sidechains known in the art of cephalosporin anti-bacterial compounds, which all have that amide linkage and remaining portion of the cephalosporin C molecule in common, would not substantially interfere with the enzymatic cleavage, and would thus be removed in a manner analogous to the removal of the 7-aminoadipoyl sidechain of cephalosporin C. Such cleavage of known 7-position sidechains may well be of value in further derivitization of known cephalosporin antibacterial compounds.

The group $R^3$ is defined to include various substituents characteristic of typical fermentation products, e.g., for cephalosporin C, $R^3$ would be $CH_2R^4$ where $R^4$ is

It is contemplated that none of the substituents defining $R_3$ would in any way interfere with the enzymatic action of the cephalosporin C amidase of the present invention, largely for the reasons discussed above.

Thus, it has been found that, in accordance with the method of the present invention, desacetoxy cephalosporin C ($R^3=CH_2R^4$ where $R^4=H$) is converted to 7-aminodesacetoxycephalosporanic acid (7-ADCA) to an extent essentially equivalent to the conversion of cephalosporin C to 7-aminocephalosporanic acid (7-ACA). This indicates that the functional group at the 3-position is not crucial to the binding of substrate to the enzyme.

The process of one-step enzymatic conversion of cephalosporin C and derivatives to 7-aminocephalosporanic acid and derivatives with which the present invention is concerned may be schematically represented as follows:

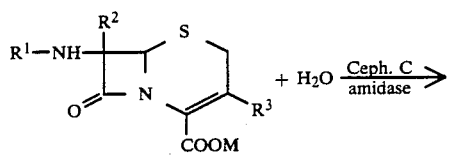

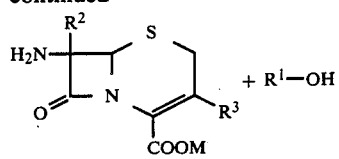

More particularly, the conversion of cephalosporin C to 7-aminocephalosporanic acid may be illustrated as follows:

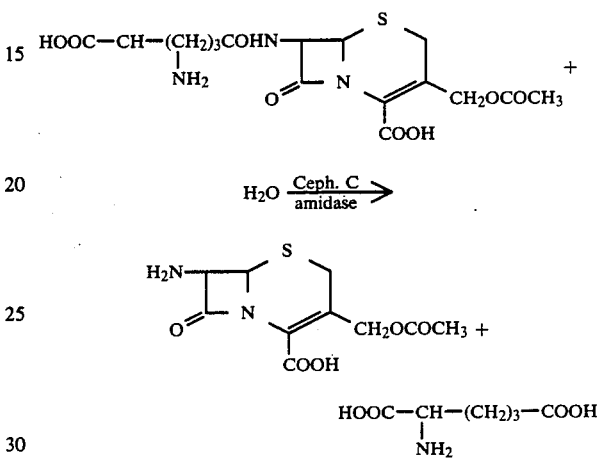

The process of the present invention may be carried out in any way which effectively brings the cephalosporin C amidase of the present invention into contact with the compounds of Formula I so that enzymatic conversion of these compounds to the compounds of Formula II can take place. This is the definition of the term "treating" in its broadest context. Ordinarily, it would be preferred to employ a cell free broth of crude cephalosporin C or derivative as the feed stream and treat it in a batch wise fashion with crude cephalosporin C amidase broth. This approach realizes the greatest efficiencies since it does not require any substantial purification of the reactants initially. Of course, modifications are possible. E.g., the reactants may be purified to whatever extent desired before being brought into contact with each other. Also, it would be possible to carry out the process in a continuous manner rather than batch wise. The contacting of the reactants themselves may be modified in various ways in keeping with advances in process technology. Thus, an immobilized enzyme column may be employed for the cephalosporin C amidase with the compound of Formula I being passed through the column. Another example of such process technology is that relating to membrane reactors. Another alternative process for contacting of the reactants would be to culture the *Arthrobacter viscosus* ATCC 53594, or descendants, in the same fermentation broth used to produce the cephalosporin C or derivative reactant. It would also be possible to modify that fermentation broth once the cephalosporin C or derivative is produced and then introduce the *Arthrobacter viscosus* ATCC 53594, or decendants, culturing it to produce the cephalosporin C amidase. This approach, however, is not likely to provide optimum yields. The preferred method of contacting the reactants is by way of the immobilized enzyme column described above.

Further below working examples describe the method currently employed to demonstrate the enzymatic deacylation of cephalosporin C, which involves a preliminary purification of the cephalosporin C amidase, largely for the purpose of increasing the concentration of enzyme and thus promoting the production of higher amounts of 7-aminocephalosporanic acid. Consequently, the method in the working examples would not necessarily be suggestive of methods which would be ulitized for commercial production.

There are techniques well known in the fermentation art for improving the yields of desired products produced by various strains of microorganisms. For example, a given producing strain may be irradiated or exposed to other stimuli known to greatly increase the ongoing mutation of the genetic material of the microorganism. By using a sensitive screen, it is then possible to select from the many mutations thus produced only those which result in an enhanced production of the desired product. In this way, it is usually possible to continually improve the output of a producing strain through its various selected decendants. With regard to the present invention, similar improvements in output of cephalosporin C amidase by selected descendants of *Arthrobacter viscosus* ATCC 53594, may be achieved. A satisfactory screen for this purpose is the use of high performance liquid chromatography which can detect the enzymatic cleavage products at very low concentrations, thus clearly establishing that cephalosporin C amidase has been produced by any particular descendant in question. It is also possible that this selection process will provide descendants which produce a more efficient cephalosporin C amidase, thus giving higher yields in the enzymatic conversion of cephalosporin C to 7-aminocephalosporanic acid. All such descendants of *Arthrobacter vicosus* ATCC 53594, are within the scope of the present invention, as are all of the more efficient cephalosporin C amidases just described.

Techniques are also now available whereby it is possible to manipulate the genetic material, i.e., the genome of a microorganism whereby all or selected portions thereof may be expressed outside the microorganism, e.g., in another microorganism such as *E. coli*. The use of restriction endonucleases makes it possible to divide up the genetic material of *Arthrobacter viscosus* ATCC 53594, or cephalosporin C amidase producing, or potentially producing descendants thereof, and recombine it with the genetic material of some other microorganism or living matter in such a way that the genetic material is expressed, i.e., proteins are assembled pursuant to the messenger RNA code to produce cephalosporin C amidase. Various introns and other genetic codes may be involved in this process, as is well understood in the art. In fact, advances in this technology may be readily adapted to such expression. For example, it may be possible to employ cell parts and mRNA, ex vivo, to achieve expression outside of a living system. The basic purpose of any of the types of expression described above, however, would be the same: to increase the amount of cephalosporin C amidase capable of being produced by the given genetic material of the *Arthrobacter viscosus* ATCC 53594, or particular descendant in question. It might also be possible, though, to change the genetic material so as to produce a more efficient cephalosporin C amidase in accordance with a specified knowledge of the overall desired binding characteristics of such an enzyme. Accordingly, any expression of the genetic material of *Arthrobacter viscosus* ATCC 53594, or any cephalosporin C amidase producing, or potentially producing descendants thereof which produces a cephalosporin C amidase of the present invention, is within the scope of the present invention.

The expression "cephalosporin C amidase producing, or potentially producing descendants" as used herein, simply reflects the fact that not all descendants will be cephalosporin C amidase producing and that these non producers form no part of the present invention, but that it is possible, on the other hand, that a non producer has genetic material which can be expressed to produce cephalosporin C amidase, but that expression does not take place because of some other feature encoded in the genetic material. Such a descendant is a "potentially producing" one and clearly does form a part of the present invention.

The strain described above has been deposited with the American Type Culture Collection (ATCC) 12301 Parklawn Dr. Rockville, Md. 20852 USA and has been assigned deposit number 53594.

In order to demonstrate the enzymatic deacylation of cephalosporin C to give 7-aminocephalosporanic acid (7-ACA), the general procedure illustrated below has been followed:

Enzyme preparation:

*slant culture washed with sterile water
↓
inoculate liquid seed medium
↓ 24 hr at 30° C.
inoculate liquid production medium
↓ 41 hr at 30° C.
harvest cell suspension and centrifuge to remove cells
↓ concentrate and partially purify activity by fractionation with (NH$_4$)$_2$SO$_4$ at 60–80% of saturation

| Assay of activity: | incubate 0.9 ml enzyme with 0.1 ml 20 mg/ml cephalosporin C; after 3 hours at 37° determine 7-ACA by HPLC assay |
|---|---|

In more particular detail, that general procedure is defined as follows:

EXAMPLE 1

Preparation and Assay of Cephalosporin C Amidase Activity from Cultures of *Arthrobacter Viscosus*

Culture Conditions

1. Strain is maintained on CM agar plates or slants of the following composition:

| component | g/l | |
|---|---|---|
| beef extract | 1.5 | |
| yeast extract | 3.0 | |
| casitone | 4.0 | medium is adjusted to |
| peptone | 6.0 | pH 6.4 before |
| glucose | 1.0 | sterilization |
| soluble starch | 20.0 | |
| agar | 15.0 | |

2. Reisolated colonies are obtained by streaking on CM plates followed by incubation for 48 hr. at 30° C. Isolated colonies are used to inoculate CM slants (8 ml per 18 mm tube) to obtain confluent growth.

3. The slant cultures are washed with 5 ml sterile distilled water to obtain a cell suspension. One ml is used to inoculate seed medium (20 ml per 250 ml Erlenmeyer flask) of the following composition:

| component | g/l | |
|---|---|---|
| beef extract | 1.5 | |
| yeast extract | 3.0 | |
| casitone | 4.0 | adjust to pH 7.0 |
| glucose | 1.0 | before sterilization |
| soluble starch | 20.0 | |

4. Following incubation at 30° C. for 24 hr on a rotary shaker (220 rpm), 1 ml of the seed culture is used to inoculate 20 ml production medium in a 250 ml Erlenmeyer flask (same composition as seed medium). Incubation on a shaker is continued for 41 hr at 30° C.

Enzyme Recovery

1. Cells from production medium are removed by centrifugation (15000×g, 15 min at 4° C.) and the supernatant fraction is collected. During each step of enzyme recovery, the preparation is maintained at 0°–4° C.

2. The volume of supernatant is measured and solid ammonium sulfate is added slowly to give 60% of saturation at 0° C. After stirring for 15 min, the mixture is allowed to sit for 30 min at 0° C.

3. The mixture is centrifuged (15000×g, 25 min at 4° C.) and the pellet is discarded. The volume of the supernatant is measured and the supernatant is brought to 80% of saturation by addition of solid ammonium sulfate while stirring at 0° C. After stirring for an additional 15 min, the mixture is allowed to sit for 1 hr at 0° C.

4. The pellet is collected by centrifugation for 25 min at 15000×g at 4° C. The pellet is resuspended in 1/20 to 1/50 volume (relative to the original volume of the culture supernatant) with buffer of the following composition: 50 mM TES/NaOH, pH 7.5 containing 0.1M NaCl, 1 mM dithiothreitol, and 5% (w/v) glycerol. If necessary, the resulting mixture is clarified by brief centrifugation and the supernatant is filtered through a 0.45 μm Nylon-66 membrane before assay of activity. If activity assays are not performed at the time of enzyme preparation, the samples may be stored for at least 3 weeks at −30° C.

Activity Assay

1. The substrate stock solution is prepared by dissolving 20 mg potassium cephalosporin C in 1 ml buffer (composition above) and filtered through a 0.45 μm Nylon-66 membrane.

2. Cephalosporin C stock solution (0.1 ml) is added to recovered enzyme (0.9 ml) and the mixture is placed in a water bath at 37° C. Following 3-6 hr incubation, formation of 7-ACA is monitored by HPLC. The following chromatography conditions are used:

| | |
|---|---|
| mobile phase | 50 mM KH$_2$PO$_4$KOH, pH 4.7 |
| flow rate | 2.0 ml/min |
| column | Nucleosil 10 C18 (Machery-Nagel), 0.4 × 25 cm |
| temperature | ambient |
| detector | 260 nm |
| sample size | 20 μl |
| instrument | Spectra-Physics or equivalent |

Retention time of 7-ACA standard is ca. 6.0 min under these conditions.

Activity Assays of Representative Preparations

1. Typically, pooled cultures from flask fermentations are used to give supernatant volumes of 350–400 ml.

2. After concentration 20 to 50 fold using the ammonium sulfate procedure described above, enzyme preparations produce 9–25 μg/ml 7-ACA in the reaction mixtures after 3 hr incubation at 37° C. Higher levels are produced with extended incubation times (up to 6 hr at 37° C.).

TABLE I
Comparison of Amidase Activity in Shake Flasks and Stirred Jar Fermentations

| Sample No. | Mode | U/ML | U/ML[a] (Normalized) |
|---|---|---|---|
| 1. | flask | 8.9 | 0.43 |
| 2. | flask | 24.9 | 0.50 |
| 3. | flask | 33.9 | 0.72 |
| 4. | flask | 36.4 | 0.73 |
| 5. | flask | 14.4 | 0.29 |
| 6. | flask | 21.5 | 0.43 |
| 7. | stirred jar[b] | 33.9 | 0.72 |
| 8. | stirred jar[b] | 38.1 | 0.76 |

[a]One unit is defined as the amount of enzyme that catalyzes the formation of 1 μg/ml 7-ACA in 3 hr at 37 C in the presence of 2 mg/ml cephalosporin C. Normalized values indicate the amount of enzyme calculated to be present in the original culture supernatant assuming complete recovery of activity during ammonium sulfate precipitation.
[b]Stirred jar fermentations used the same production medium as flask fermentations (10 l per 15 l jar).

[a]One unit is defined as the amount of enzyme that catalyzes the formation of 1 μg/ml 7-ACA in 3 hr at 37° C. in the presence of 2 mg/ml cephalosporin C. Normalized values indicate the amount of enzyme calculated to be present in the original culture supernatant assuming complete recovery of activity during ammonium sulfate precipitation.

[b]Stirred jar fermentations used the same production medium as flask fermentations (10 l per 15 l jar).

The higher production levels in the stirred jar fermenter will be noted. It is anticipated that enzyme production in stirred jars would be required for industrial application of the present invention.

EXAMPLE 2

Desacetoxycephalosporin C (DOAC)
7-Aminodesacetoxycephalosporanic Acid (7-ADCA)

As already described above, desacetoxycephalosporin C (DOAC) may be converted to 7-aminodesacetoxycephalosporanic acid (7-ADCA) using the enzyme and method of the present invention. This conversion may be illustrated as follows:

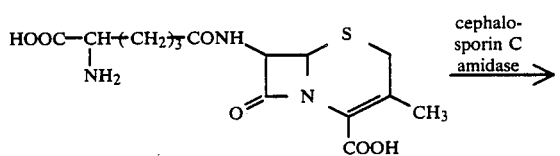

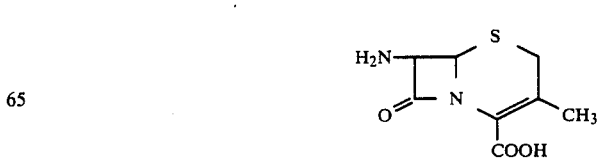

Cephalosporin C amidase, prepared as described above in Example 1, was incubated with 2 mg/ml DAOC for 3 hrs at 37° C. The reaction mixture required a pre-chromatography separation step using XAD-16® (Rohm and Haas) macroreticular water insoluble cross linked adsorbent polymer to remove coeluting contaminants. Chromatography was carried out in accordance with the procedures described above in Example 1 (except that the mobile phase consisted of 1 liter deionized water, 1.88 g hexyl sodium sulfonate, 2.025 ml phosphoric acid, and 25 ml acetonitrile, pH 2.75), and established that approximately 0.5 to 1.0% of the original DOAC substrate had been converted to 7-ADCA.

EXAMPLE 3

One-step Enzymatic Conversion of Cephalosporin C to 7-Aminocephalosporanic Acid: Direct Measurement of the Cleavage Products In order to provide further evidence that the conversion of cephalosporin C to 7-aminocephalo sporanic acid (7-ACA) in accordance with the present invention is indeed a one-step process accomplished by a single enzyme (cephalosporin C amidase), cleavage was carried out as described above in Example 1; but in addition to measuring formation of 7-ACA by HPLC as described in Example 1, the appearance of the other cleavage product, aminoadipic acid, was measured as well. This was done using a Beckman 6300 High Performance Analyzer. The enzyme was incubated with cephalosporin C (2 mg/ml final concentration) for 4 hours at 37° C. The results are illustrated in the table of values below.

TABLE II

Concentrations of Aminoadipic Acid and 7-ACA Isolated from Incubations of Cephalosporin C with Amidase Enzyme from *Arthrobacter viscosus*

| Sample No. | Aminoadipic Acid μg/ml | 7 ACA μg/ml | Moles aminoadipic acid moles 7-ACA |
|---|---|---|---|
| 1 | 22 | 30 | 1.2 |
| 2 | 19 | 29–42* | 1.1–0.7* |

*The 7-ACA analysis on this sample was performed on very dilute solutions making the confidence level for 7-ACA quantification lower than the other sample.

The one to one molar ratio of isolated products is good evidence for a one step conversion of cephalosporin C to 7-ACA by the amidase enzyme.

What is claimed is:

1. A process for the one step conversion of cephalosporin C and derivatives thereof to the corresponding 7-aminocephalosporanic acid and derivatives comprising treating said cephalosporin C and derivatives with a cephalosporin C amidase derived from *Arthrobacter viscosus* ATCC 53594, or from any cephalosporin C amidase producing, or potentially producing descendants thereof, cephalosporin C amidase producing.

2. A process for the one step conversion of cephalosporin C and derivatives thereof of the formula:

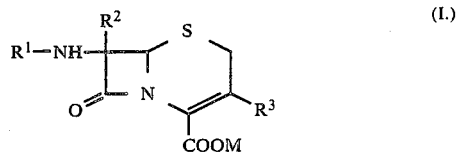

where
R$^1$ is

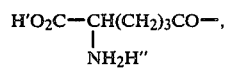

R$^2$ is —H;
R$^3$ is —H or

or CH$_2$R$^4$, where R$^4$ is —H, —OH, or

and
M is ⊖; —H; alkali metal or other pharmaceutically acceptable salt; pharmaceutically acceptable ester; or readily removable carboxyl protecting group;
to a 7-aminocephalosporanic acid of the formula:

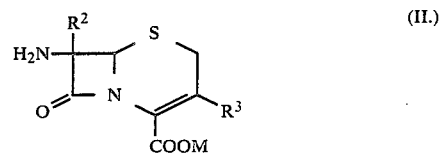

COMPRISING:
treating a compound of Formula I with an enzyme, cephalosporin C amidase, capable of converting a compound of Formula I to a compound of Formula II in one-step; said enzyme CHARACTERIZED BY having been derived from *Arthrobacter viscosus* ATCC 53594, or from any cephalosporin C amidase producing, or potentially producing descendants thereof.

3. A process according to claim 2 wherein the compound of Formula I is cephalosporin C and the compound of Formula II is 7-aminocephalosporanic acid.